United States Patent [19]

Pelah et al.

[11] Patent Number: 5,204,414

[45] Date of Patent: Apr. 20, 1993

[54] SALTS OF POLYALKYL VINYL ETHER MALEIC ANHYDRIDE AND DENTAL PROSTHESIS ADHESIVE PRODUCED THEREFROM

[75] Inventors: Zvi Pelah, Savyon, Israel; Ernst Urmann, Ludwigshafen; Werner Kopp, Harthausen, both of Fed. Rep. of Germany

[73] Assignee: Giulini Chemie GmbH, Ludwigshafen, Fed. Rep. of Germany

[21] Appl. No.: 548,376

[22] Filed: Jul. 5, 1990

[30] Foreign Application Priority Data

Jul. 6, 1989 [DE] Fed. Rep. of Germany ....... 3922170

[51] Int. Cl.$^5$ .......................... C08F 8/44; C08F 20/08; C08F 20/66; C08F 222/02
[52] U.S. Cl. ............................... 525/327.8; 525/328.9; 526/271; 526/318.2; 523/118; 523/120
[58] Field of Search ............... 525/327.2, 327.8, 328.9; 526/271, 318.2; 523/118, 120

[56] References Cited

U.S. PATENT DOCUMENTS

| | | | |
|---|---|---|---|
| 3,511,798 | 5/1970 | Isaacson et al. | 525/327.8 |
| 4,758,630 | 7/1988 | Shah et al. | 525/328.9 |
| 4,929,690 | 5/1990 | Goertz et al. | 525/327.8 |

OTHER PUBLICATIONS

A brochure entitled "Aerosil", a product of the Degussa Company.

Primary Examiner—Paul R. Michl
Assistant Examiner—LaVonda DeWitt
Attorney, Agent, or Firm—Spencer, Frank & Schneider

[57] ABSTRACT

Salts of lower alkyl vinyl ether/maleic anhydride are described as active components in dental adhesives. A process for the preparation of these salts is described.

The salts are partially neutralized mixed salts of lower alkyl vinyl ether/maleic anhydride copolymers. The neutralization of the copolymer is effected with aluminum, and calcium and/or sodium.

8 Claims, No Drawings

SALTS OF POLYALKYL VINYL ETHER MALEIC ANHYDRIDE AND DENTAL PROSTHESIS ADHESIVE PRODUCED THEREFROM

CROSS REFERENCE TO RELATED APPLICATION

This application is related to Application No. 39 22 170.9 filed Jul. 6, 1989 in the Patent Office of the Federal Republic of Germany, the entire disclosure of which is incorporated herein by reference.

BACKGROUND OF THE INVENTION

1. Field of the Invention

The present invention relates to novel mixed salts of polyalkyl vinyl ether maleic anhydride and their use in dental adhesives to secure dental prostheses, and a process for their preparation.

2. Technology Review

Commercially available dental adhesives are sold as powders, creams or liquids. The essential function of dental adhesives is to give the prosthesis the most secure seat and the best possible adhesion. Saliva plays an important role in the adhesion process because in the presence of saliva the adhesive must establish a connection between the prosthesis and the palate by generating cohesive and adhesive forces. Therefore, adhesives must contain substances which swell upon contact with saliva and form an elastic film on the base of the proshesis. Substances suitable as adhesives must not irritate mucous membranes, and must be toxicologically acceptable, particularly with respect to heavy metals since these may enter the gastro-intestinal tract together with the saliva. Further, substances suitable as adhesives must not contain any harmful microbiological impurities or contaminants and must not chemically react with the prosthesis material. Finally, suitable adhesives should be free of annoying odors and taste, and provide the longest possible duration of adhesion while being safely removable from the palate and from the prosthesis without leaving residues.

In the past, natural swellable substances were used as adhesives. These were natural polymers, e.g. polysaccharides, which with water form highly viscous solutions or suspensions that have elastic properties. In modern formulations, synthetic polymers are combined with these natural substances or are employed alone.

For example, published application DE-OS 1,909,209 discloses a natural polymer, tragacanth, or karaya gum in combination with sodium methyl cellulose as the adhesive component. The natural polymer, tragacanth, swells in the aqueous environment of the mouth and is able to promote adhesion only in this state. A drawback is that the magnitude of the adhesive force is dependent on the quantity of saliva in the each individual's mouth so that the adhesive force is different from user to user.

Published application DE-OS 2,025,268, which appears to correspond to U.S. Pat. No. 3,575,915, discloses a dental adhesive cream which contains polyvinyl acetate and a softener as its adhesive component. The softener makes it difficult to remove the adhesive cream from the prosthesis for cleaning purposes and has an irritating effect on the mucous membranes of the oral cavity. Moreover, if the cream contains too much softener, it becomes too soft and its adhesion is insufficient even for normal stresses.

Published application DE-OS 1,467,795 discloses an adhesive cream in which polyvinyl pyrrolidone is employed as the adhesive component. A grave drawback of this adhesive cream is that the additives employed to neutralize its taste, particularly citrate derivatives, adversely influence the taste sensation.

The production and use of mixed Ca/Na salts of the maleic acid anhydride/methyl vinyl ether copolymer is disclosed in U.S. Pat. No. 3,003,988. This powdered material is very well suited as an adhesive component in adhesives; however, it has the decisive drawback that noticeable fluctuations in adhesion may occur due to the process used to dry the salt.

In published application DE-OS 2,133,709, the drawbacks mentioned above of U.S. Pat. No. 3,003,988 are purportedly removed. This published application teaches that the powdered copolymer salt produces its best adhesion only if it is dried in a fluidized bed furnace. Its maximum adhesion is attained if the moisture content of the powdered salt lies at 10%±1% and is kept constant.

A process for manufacturing the basic polymer maleic anhydride (MA)/methyl vinyl ether (MVE) employed for the salt formation in published application DE-OS 2,133,709 and U.S. Pat. No. 3,003,988 may be found in U.S. Pat. No. 2,782,182 and U.S. Pat. No. 2,047,398, incorporated herein by reference. The radical polymerization of the monomers, maleic anhydride and methyl vinyl ether occurs in a solvent, for example benzene or methylene chloride, and is possible only when benzene is used to obtain an end product which has a sufficiently high degree of polymerization. After drying, the copolymer produced contains large quantities of benzene which cannot be removed by distillation or simple drying. Therefore, these polymers cannot be employed for the production of the respective Ca/Na salts. In some countries, it is forbidden by law to use such materials for medical/cosmetic applications such as dental adhesives.

An improved method of producing the respective copolymers free of benzene was developed by the assignee of the present invention and is disclosed in published application DE-OS 3,712,265. Such material is particularly suitable for the production of the novel Al/Ca/Na salts according to the present invention and also for the Ca/Na salts disclosed in U.S. Pat. No. 3,003,988 and in published application DE-OS 2,133,709.

European Patent Publication No. EP A2 0,265,916, which appears to correspond to U.S. Pat. No. 4,758,630, reports dental adhesives which contain zinc and/or strontium salts of the MA/MVE copolymer in addition to the Ca/Na salt of this copolymer. The zinc salt is preferred in the adhesives disclosed. If the adhesive contains either the zinc or the strontium salt, and also the calcium/sodium salt of the MSA/MVE copolymer, the adhesive effect is purported to be substantially better than in formulations containing only the Ca/Na salt. A serious drawback of this adhesive is that it contains the toxic metals zinc and strontium. Additionally, the salt produced according to Example 1 of European Patent No. EP A2 0,256,916 must be dried for 16 to 18 hours at 70° C. The long drying time and the use of highly diluted aqueous suspension in the manufacturing process for these zinc and strontium salts are uneconomical.

It is the object of the invention to provide adhesive components for dental adhesives that exhibit substantially improved adhesion, do not contain any physiologically objectionable heavy metals, and can be manufactured economically.

SUMMARY OF THE INVENTION

Novel salts of lower alkyl ($C_{1-4}$) vinyl ether/maleic copolymers are provided which include the following structural unit:

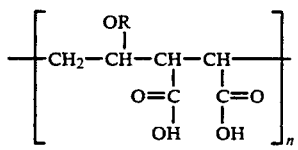

where R is an alkyl radical having 1 to 4 carbon atoms, n is an integer greater than 0, with n being selected so that the specific viscosity of the corresponding anhydride lies at 2.6 to 3.5. A total of 30 to 95% of the carboxyl groups are neutralized by aluminum, calcium or sodium. The pH of the salts lies between 6.5 and 7.5. The Al:Ca ratio in the salt lies between 1:1 and 1:4. The novel mixed Al/Ca/Na salts of the lower alkyl vinyl ether/maleic anhydride are employed as an active compound in dental adhesives.

DETAILED DESCRIPTION OF THE INVENTION

The present invention provides novel salts of lower alkyl vinyl ether/maleic acid copolymers which include the following repeating structural unit:

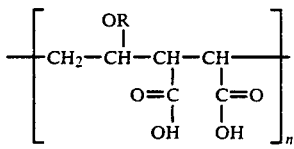

where R is an alkyl radical having 1 to 4 carbon atoms, n is an integer greater than 0, with n being selected so that the specific viscosity of the corresponding anhydride lies at 2.6 to 3.5. A total of 30 to 95% of the carboxyl groups are neutralized by aluminum, calcium or sodium. The pH of the salts lies between 6.5 and 7.5. The Al:Ca molar ratio in the salt lies between 1:1 and 1:4. The novel mixed Al/Ca/Na salts of the lower alkyl vinyl ether/maleic anhydride are employed as an active compound in dental adhesives.

According to one embodiment, the carboxyl groups are neutralized only with the aluminum cation, with R representing methyl. This Al salt of the MA/MVE copolymer according to Example 4 may be used as the starting composition for the production of the Al/Ca/Na salt according to the invention.

The novel Al/Ca/Na salts of the copolymer MA/MVE are suitable for the production of dental adhesives. Moreover, additives employed in this connection, such as, for example, Vaseline ®, Aerosil ™ and the like, are substances that are known in the art. Compared to commercially available adhesive formulations, dental adhesives containing the novel Al/Ca/Na salt of the MA/MVE copolymer as the adhesive component exhibit a significantly improved and constant adhesion.

A decisive advantage of the salts according to the present invention is that the metal ion component $Al^{3+}$ is physiologically more acceptable than the corresponding zinc or strontium salts described in EP A2 0,265,916. It is also known that aluminum salts have a bactericidal effect. This is a particular advantage in products designed for us in the oral region because this region is constantly inhabited by many germs.

The novel salts can be prepared by several methods. A starting product for the production of the Al/Ca/Na salt according to the invention may be the Ca/Na salts of copolymers whose production is disclosed, for example, in U.S. Pat. No. 3,003,988, incorporated herein by reference. The salts preferred there are partially neutralized Ca/Na salts of MA/AVE copolymers in which R represents methyl and which have a degree of neutralization of about 64 to 80% and a Ca/Na ratio of 2.5:1 to 4:1 (Examples 6 and 7). Generally their pH lies between 6 and 7.5. According to U.S. Pat. No. 3,003,988, any other Ca/Na salts having a Ca:Na ratio from 1:1 to 5:1 can also be employed.

Furthermore, the salts according to published application DE-OS 2,133,709 in which some of the carboxyl groups that are not bound to sodium or calcium are esterified can also be employed.

Additionally it is also possible to produce the salts according to the present invention from the copolymer maleic anhydride/methyl vinyl ether (MA/MVE) which is commercially available, for example, under the trade name Gantrez AN 169 ® made by GAF. This is a high molecular weight copolymer having a specific viscosity of 2.6 to 3.5. It is also possible to start with derivatives of Gantrez AN 169 ® in which all anhydride groups are hydrolized. This likewise high molecular acid is commercially available under the trade name Gantrez S 97 ®. The MA/MVE copolymers obtainable according to the process disclosed in Patent No. 3,712,265 of the Federal Republic of Germany are particularly suitable for the production of the salts according to the invention. Regardless of which starting material is used, it is important to know its composition and particularly its Ca/Na ratio and its degree of neutralization.

The remaining starting materials required for the production of the salts according to the invention, in the case of the anhydride and the acid, are known, well-defined substances, e.g. sodium hydroxide solution, calcium hydroxide and others. Suitable aluminum components are, for example: aluminum triisopropylate in which aluminum is contained as a three-valent cation. This compound is commercially available. Also, a freshly precipitated, still active aluminum hydroxide having an $Al_2O_3$ content of, for example, 70% can be employed. In principle, all aluminum containing salts containing $Al^{3+}$ cations in solution can be employed; however, aluminum containing salts which contain toxic or skin-irritating anions, for example chloride, nitrate, sulfate and others, should not be employed or should be employed and carefully removed once the end product is manufactured.

The production of the copolymer salts according to the invention will now be described in greater detail with reference to the following examples.

EXAMPLE 1

2000 ml isopropanol are put into a vessel equipped with a stirrer and 562 g polymethyl vinyl ether/maleic anhydride having a specific viscosity of 2.6 to 3.5 (obtainable from GAF under the trade name Gantrez AN 169 ®) and 133 g calcium hydroxide as well as 61.8 g Al-triisopropylate are added. This mixture is stirred well for half an hour, whereupon 36 g of sodium hydroxide flakes, dissolved in 100 ml water, are trickled in under stirring during a period of 30 to 60 minutes. During the developing reaction, the temperature rises to 36° to 38° C. and is raised further by heating to 50° C. The mixture is stirred at this temperature until the pH has reached 7. After cooling, the suspension is filtered out through a suction filter and, after drying at a temperature of 100° C., is ground and screened to $<50 \mu$.

A 1:4:1 Al/Ca/Na salt is obtained which contains 25% free and esterified carboxyl groups.

EXAMPLE 2

2000 ml isopropyl alcohol are put into the vessel of Example 1 and 609 g maleic acid /methyl vinyl ether copolymer (high molecular weight copolymer, e.g. Gantrez S-97 by GAF) are suspended under stirring, and then 104 g $Ca(OH)_2$ and 51 g of a reactive aluminum hydroxide ($Al_2O_3$ content: 70%) are added, likewise under stirring. Thereafter, the temperature is raised to about 43° to 45° C. and 56 g NaOH in 100 ml water are added to it within half an hour. The temperature, which still rises somewhat, is kept constant at 50° C. until the pH of the suspension has dropped to 7. Then the mixture is filtered through a suction filter, is washed with some isopropanol and is dried at about 70° to 80° C. The product is then ground and screened to $<50\mu$.

The result is an 1.5:2:1 Al/Ca/Na salt which has a degree of neutralization of 90%.

EXAMPLE 3

3000 ml isopropyl alcohol are used to suspend, under stirring, 683 g of a 3.5:1 Ca/Na salt of MA/MVE copolymer having a degree of neutralization of 54%. Under intensive stirring, 114 g aluminum triisopropylate are then added and the temperature is raised to 60° C. The pH thus drops from an initial 9 to 10 to a value of 7, with the reaction being terminated by cooling and removing of the isopropanol. The filter cake is processed in the manner described in Examples 1 and 2.

The result is a 2:3.5:1 Al/Ca/Na salt having a degree of neutralization of 78%.

EXAMPLE 4

1000 ml isopropanol are used to suspend, under stirring, 200 g of a maleic acid /methyl vinyl ether copolymer (high molecular weight copolymer, e.g. Gantrez S 97 made by GAF). Under intensive stirring, 114 g aluminum triisopropylate are then added and the mixture is heated to 60° C. Under stirring, the temperature is kept constant for one hour. After cooling, the suspension is filtered, dried in a drying cabinet at about 70° to 80° C., ground and screened to $<50\mu$.

The result is an Al salt of the MA/MVE copolymer having a degree of neutralization of 73%.

100 g of this salt are intensively mixed with 225 g of a 3.5:1 Ca/Na salt of the same copolymer (80% neutralized) which is likewise ground and screened to $<50\mu$. The result is a 2:3.5:1 Al/Ca/Na salt of the MA/MVE copolymer having an average degree of neutralization of 78%.

With respect to its Ca, Na and Al content as well as its degree of neutralization, this salt is identical with the product produced in Example 3. The only difference between the two products is the cation distribution within the polymer.

EXAMPLE 5

420 l isopropanol are presented in a 1000 l horizontal mixer (a Drais mixer) and 120.5 kg of a 3.5:1 Ca/Na salt having a degree of neutralization of 67.5% are suspended therein. Likewise under stirring, 12.3 kg aluminum triisopropylate are added, and after 30 minutes of mixing, the temperature is raised to 55° C. After an hour's stirring at this temperature—the pH should now lie between 7 and 7.5—distillation of the isopropanol begins.

The fluidized bed drying process is continued under a vacuum (200 to 250 mbar) until all of the isopropanol has been removed. The product temperature should here not exceed 70° C.

The thus uniformly dried product generally breaks up into a fine powder and is then ground to realize a grain size of less than $50\mu$.

The result is a 1:3.5:1 Al/Ca/Na salt of the MA/MVE copolymer having a degree of neutralization of 82.5%.

EXAMPLE 6

Two adhesive cream formulations are produced which differ only in their copolymer components. In formulation A, a Ca/Na salt of the copolymer MA/MVE is employed, in formulation B the Al/Ca/Na salt of the copolymer MA/MVE.

| Composition Formulation | weight percent in | |
| --- | --- | --- |
|  | A | B |
| mineral oil | 37 | 37 |
| Vaseline-brand petroleum jelly | 12 | 12 |
| Aerosil-brand ($SiO_2$-Degussa) | 1 | 1 |
| 3.5:1 Ca/Na salt of MA/MVE copolymer (78%) neutralized | 50 | — |
| 2:3.5:1 Al/Ca/Na salt of MA/MVE copolymer (78% neutralized) | — | 50 |
|  | 100 | 100 |

EXAMPLE 7

The adhesive force of the adhesive cream formulations from Example 6 is tested with the aid of the apparatus disclosed in published application 2,133,709. Water is added here in increasing quantities (in 0.5 g increments) to 0.5 g of the adhesive cream:

|  | without water | +0.5 g water | +1 g water | +1.5 g water | +2 g water |
| --- | --- | --- | --- | --- | --- |
| adhesive force of 6A [$kg/cm^2$] | 1.27 | 2.19 | 4.02 | 3.87 | 2.91 |
| adhesive force of 6B [$kg/cm^2$] | 1.29 | 3.52 | 4.61 | 4.47 | 3.85 |

While the invention has been described in connection with specific embodiments thereof, it will be understood that it is capable of further modification and this application is intended to cover any variations, uses, or adaptations of the invention following, in general, the principles of the invention and including such departures from the present disclosure as come within known or customary practice within the art to which the invention pertains and as may be applied to the essential features hereinbefore set forth, and as follows in the scope of the appended claims.

What is claimed is:

1. In a dental prosthesis adhesive the improvement comprising a mixed partially neutralized salt of alkyl vinyl ether/maleic anhydride copolymers including the following structural unit

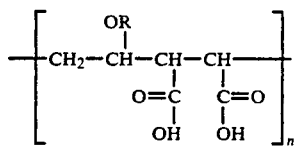

where R represents an alkyl radical having 1 to 4 carbon atoms, 30 to 95% of the carboxyl groups are neutralized with aluminum, and at least one of calcium and sodium, the pH of the salts is between about 6.5 and 7.5 and n is an integer greater than zero, and n is selected so that the specific viscosity of the corresponding anhydride is between about 2.6 and 3.5 and the Al:Ca ratio is between about 1:1 and 1:4.

2. In a dental prosthesis adhesive the improvement comprising a mixed partially neutralized salt of alkyl vinyl ether/maleic anhydride copolymers recited in claim 1, wherein R represents methyl.

3. A mixed partially neutralized salts of alkyl vinyl ether/maleic anhydride copolymers including the following structural unit

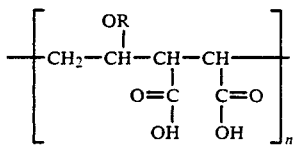

where R represents an alkyl radical having 1 to 4 carbon atoms, 30 to 95% of the carboxyl groups are neutralized with aluminum and at least one of calcium and sodium, the pH of the salts is between about 6.5 and 7.5 and n is an integer greater than zero, and n is selected so that the specific viscosity the corresponding anhydride is between about 2.6 and 3.5 and the Al:Ca ratio is between about 1.1 and 1.4.

4. The mixed partially neutralized salts of alkyl vinyl ether/maleic anhydride copolymers recited in claim 3, wherein R represents methyl.

5. A process for the preparation of a mixed partially neutralized salt of methyl vinyl ether/maleic anhydride copolymer including the following structural unit

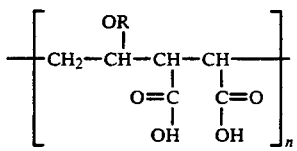

where R represents methyl, 30 to 95% of the carboxyl groups are neutralized with aluminum, calcium and sodium, the pH of the salts is between about 6.5 and 7.5 and n is an integer greater than zero, and n is selected so that the specific viscosity of the corresponding anhydride is between about 2.6 and 3.5 and the Al:Ca ratio is between about 1:1 and 1:4, comprising:

neutralizing the carboxyl groups of a methyl vinyl ether/maleic anhydride copolymers with an aluminum compound to produce an aluminum salt of the methyl vinyl ether/maleic acid anhydride copolymer; and reacting said partially neutralized aluminum salt of methyl vinyl ether/maleic anhydride copolymer with a Ca/Na salt of the same copolymer in an alcohol reaction medium to produce a mixed partially neutralized salts of methyl vinyl ether/maleic anhydride copolymers including the following structural unit

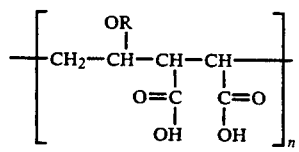

where R represents methyl, 30 to 95% of the carboxyl groups are neutralized with aluminum, calcium and sodium, the pH of the salts is between about 6.5 and 7.5 and n is an integer greater than zero, and n is selected so that the specific viscosity of the corresponding anhydride is between about 2.6 and 3.5 and the Al:Ca ratio is between about 1:1 and 1:4.

6. A process for the preparation of a mixed partially neutralized salt of alkyl vinyl ether/maleic anhydride copolymers, including the following structural unit

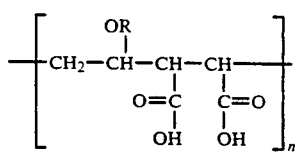

where R represents an alkyl radical having 1 to 4 carbon atoms, 30 to 95% of the carboxyl groups are neutralized with aluminum, calcium and sodium, the pH of the salts is between about 6.5 and 7.5 and n is an integer greater than zero, and n is selected so that the specific viscosity of the corresponding anhydride is between about 2.6 and 3.5 and the Al:Ca ratio is between about 1:1 and 1:4, comprising:

reacting alkyl vinyl ether/maleic anhydride copolymers with calcium, aluminum, and sodium compounds in an alcohol reaction medium to produce said mixed partially neutralized salt of alkyl vinyl ether/maleic anhydride copolymers.

7. A process for the preparation of a mixed partially neutralized salt of alkyl vinyl ether/maleic anhydride copolymers according to claim 6, wherein said alkyl vinyl ether/maleic anhydride copolymer is methyl vinyl ether/maleic anhydride, and R is methyl.

8. A process for the preparation of a mixed partially neutralized salts of alkyl vinyl ether/maleic anhydride copolymers, including the following structural unit

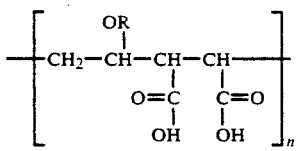

where R represents an alkyl radical having 1 to 4 carbon atoms, 30 to 95% of the carboxyl groups are neutralized with aluminum, calcium and sodium, the pH of the salts is between about 6.5 and 7.5 and n is an integer greater than zero, and n is selected so that the specific viscosity of the corresponding anhydride is between about 2.6 and 3.5 and the Al:Ca ratio is between about 1:1 and 1:4, comprising:

reacting Ca/Na salts of alkyl vinyl ether/maleic anhydride copolymers with an aluminum compound in an alcohol reaction medium to produce said mixed partially neutralized salts of alkyl vinyl ether/maleic acid anhydride copolymers.

* * * * *